(12) United States Patent
Zhang et al.

(10) Patent No.: US 7,795,201 B2
(45) Date of Patent: Sep. 14, 2010

(54) PERSONAL CARE COMPOSITIONS

(75) Inventors: Xiaodong Zhang, Livingston, NJ (US); Jerry R. Conklin, Midland, MI (US)

(73) Assignee: Dow Global Technologies

( * ) Notice: Subject to any disclaimer, the term of this patent is extended or adjusted under 35 U.S.C. 154(b) by 426 days.

(21) Appl. No.: 11/792,257

(22) PCT Filed: Oct. 31, 2005

(86) PCT No.: PCT/US2005/039379

§ 371 (c)(1), (2), (4) Date: Jun. 1, 2007

(87) PCT Pub. No.: WO2006/076065

PCT Pub. Date: Jul. 20, 2006

(65) Prior Publication Data

US 2008/0206168 A1  Aug. 28, 2008

(51) Int. Cl.
  *C11D 3/02* (2006.01)
  *C11D 7/02* (2006.01)

(52) U.S. Cl. ............... 512/1; 424/70.1; 424/70.13; 424/401; 510/108; 510/119; 510/130; 510/461; 510/470; 510/473; 512/2; 512/3; 514/781

(58) Field of Classification Search ............... 424/70.1, 424/70.13, 401; 510/108, 119, 130, 461, 510/470, 473; 512/1, 2, 3; 514/781
See application file for complete search history.

(56) References Cited

U.S. PATENT DOCUMENTS

| 4,645,812 | A | 2/1987 | Maier |
|---|---|---|---|
| 5,432,215 | A | 7/1995 | Girg |
| 6,156,713 | A | 12/2000 | Chopra et al. |
| 6,172,037 | B1 | 1/2001 | Perring et al. |
| 2003/0086953 | A1 | 5/2003 | Ricca |
| 2003/0166497 | A1 * | 9/2003 | Yang et al. ............ 512/1 |
| 2003/0211061 | A1 | 11/2003 | Deckner et al. |
| 2004/0087476 | A1 | 5/2004 | Dykstra et al. |

FOREIGN PATENT DOCUMENTS

| EP | 556957 | | 8/1993 |
|---|---|---|---|
| WO | WO 91/13138 | * | 9/1991 |
| WO | WO 98/00494 | | 1/1998 |
| WO | WO 99/44568 | | 9/1999 |
| WO | WO 00/35416 | | 6/2000 |
| WO | WO 03/075879 | | 9/2003 |
| WO | WO 2004/105723 | | 12/2004 |

OTHER PUBLICATIONS

M. Rieger, et al., (Eds): "*Surfactants in Cosmetics*", Surfactant Science Series, vol. 68, ed. 2., 1997, Marcel Dekker, USA 229120, pp. 48-52.
"*Perfume and Flavor Chemicals*", vols. I and II, S. Arctander, Allured Publishing, 1994, ISBN 0-931710-35-5.

* cited by examiner

*Primary Examiner*—Johann R Richter
*Assistant Examiner*—David M Browe

(57) ABSTRACT

The deposition of a benefit agent on a substrate after treatment of the substrate with a personal care composition which has a viscosity of at least 50 mPa·s at 25° C. and comprises the benefit agent and a low molecular weight surfactant is improved when a water-soluble polymer is used as a substitute for at least a portion of the low molecular weight surfactant. The headspace concentration of a fragrance provided by such personal care composition is also increased.

7 Claims, No Drawings

PERSONAL CARE COMPOSITIONS

FIELD OF THE INVENTION

The present invention relates to a method of improving the deposition of a benefit agent on a substrate that has been treated with a personal care composition and to a method of increasing the headspace concentration of a fragrance provided by a personal care composition.

BACKGROUND OF THE INVENTION

The noticeable content of benefit agents, particularly perfumes or flavors, significantly influence the consumers' decision whether to buy a personal care composition or not. The noticeable content of perfumes or flavors, herein collectively designated as fragrance, is of most importance at two places. First, the headspace concentration of the fragrance, that means the concentration in the volume left at the top of a container filled with the personal care composition, is of high importance. The fragrance concentration in the headspace is directly noticeable by the consumer before and during the use of the personal care composition. Second, the fragrance that is left on the substrate after the use of the composition, for example on hair or skin, is of high importance to consumers. In the second case, the amount of other benefit agents that are left after the use of the composition on the substrate is also important. Among others the deposition of a sunscreen agent, a moisturizing agent, or an emollient on hair or skin is of high importance. These factors significantly influence the consumers' decision whether to buy the composition or not. Much research effort has been spent on increasing the noticeable fragrance content in consumer products without undue increase of costs.

U.S. Pat. No. 6,172,037 discloses a perfume fixative for enhancing the perfume life. The perfume fixative consists essentially of polyvinylpyrrolidone, hydroxypropyl cellulose and hydrophobic oil. The polyvinylpyrrolidone and hydroxypropyl cellulose together should not constitute more than about 0.5 percent, by weight of the perfume-containing product. The perfume fixative is intended for perfumed leave-on skin products, particularly ethanol-based (deo)colognes, personal perfumes, antiperspirant deodorants and hair colognes.

The published U.S. Patent Application No. 2004/0087476 discloses a benefit agent delivery system for delivering a benefit agent to a substrate. The benefit agent delivery system comprises polymer particles and a benefit agent, such as a perfume. The polymer particles are water-insoluble and have an average particle size of from 100 nm to 50 micrometers. Disclosed polymer particles are polystyrene and poly(methyl methacrylate-dimethyl amino ethyl methacrylate) copolymer. The Patent Application discloses the importance of adding the polymer particles and the benefit agent separately to a matrix to form the benefit agent delivery system.

Many personal care compositions comprise low molecular weight surfactants for cleansing purposes, as a foaming agent, for increasing the viscosity of the composition or a combination thereof. An increased viscosity is desired for many applications to facilitate the handling of the composition and to extend the contact time between the composition and the substrate to which the composition is applied, such as skin or hair.

One object of the present invention is to find a method of improving the deposition of a benefit agent on a substrate after treatment of the substrate with a water-based personal care composition.

Another object of the present invention is to find a method of increasing the headspace concentration of a fragrance provided by a water-based personal care composition.

It has surprisingly been found that these objects can be achieved in a simple manner in water-based personal care compositions which have a viscosity of at least 50 mPa·s at 25° C. and comprise the benefit agent and a low molecular weight surfactant if at least a portion of the low molecular weight surfactant is replaced by a water-soluble polymer.

SUMMARY OF THE INVENTION

One aspect of the present invention is a method of improving the deposition of a benefit agent on a substrate after treatment of the substrate with a water-based personal care composition having a viscosity of at least 50 mPa·s at 25° C. and comprising the benefit agent and a low molecular weight surfactant, which method comprises incorporating a water-soluble polymer in the personal care composition as a substitute for at least a portion of the low molecular weight surfactant.

Another aspect of the present invention is a method of increasing the headspace concentration of a fragrance provided by a water-based personal care composition having a viscosity of at least 50 mPa·s at 25° C. and comprising the fragrance and a low molecular weight surfactant, which method comprises incorporating a water-soluble polymer in the personal care composition as a substitute for at least a portion of the low molecular weight surfactant.

Another aspect of the present invention is the use of a water-soluble polymer for improving the deposition of a benefit agent on a substrate after treatment of the substrate with a personal care composition having a viscosity of at least 50 mPa·s at 25° C. and comprising the benefit agent and a low molecular weight surfactant, wherein the water-soluble polymer is used as a substitute for at least a portion of the low molecular weight surfactant.

Another aspect of the present invention is the use of a water-soluble polymer for increasing the headspace concentration of a fragrance provided by a water-based personal care composition having a viscosity of at least 50 mPa·s at 25° C. and comprising the fragrance and a low molecular weight surfactant, wherein the water-soluble polymer is used as a substitute for at least a portion of the low molecular weight surfactant.

DETAILED DESCRIPTION OF THE INVENTION

The personal care composition is water-based. Generally, the water content of the composition is at least 30 percent, preferably at least 50 percent, more preferably at least 80 percent, based on the total weight of the composition. The composition has a viscosity of at least 50 mPa·s, typically at least 500 mPa·s, preferably at least 1,000 mPa·s, more preferably at least 2,000 mPa·s, most preferably at least 5,000 mPa·s. The composition generally has a viscosity of up to 150,000 mPa·s, preferably up to 100,000 mPa·s, more preferably up to 50,000 mPa·s. The viscosity is measured at 25° C. using a Brookfield viscometer. The method of the present invention is particularly useful for hair care and skin care compositions.

In many known personal care compositions the concentration of a low molecular weight surfactant is chosen such that the above-mentioned viscosity of the personal care composition is achieved due to the presence of the low molecular weight surfactant alone. The term "a water-soluble polymer is incorporated in the personal care composition as a substitute for at least a portion of the low molecular weight surfactant" means that the concentration of low molecular weight surfactant in the composition is lower than is needed to achieve a viscosity of the composition of at least 50 mPa·s, typically at least 500 mPa·s, preferably at least 1,000 mPa·s, more preferably at least 2,000 mPa·s, most preferably at least 5,000 mPa·s and that such lower concentration of low molecular weight surfactant is compensated by including a sufficient amount of water-soluble polymer in the composition such that the viscosity of the resulting composition is at least 50 mPa·s, typically at least 500 mPa·s, preferably at least 1,000 mPa·s, more preferably of at least 2,000 mPa·s, most preferably at least 5,000 mPa·s.

Preferably at least 20 percent, more preferably at least 30 percent, most preferably at least 40 percent of the low molecular weight surfactant that is typically included in a personal care composition to obtain the above-mentioned viscosity is replaced by a water-soluble polymer to prepare a modified personal care composition. Preferably up to 85 percent, more preferably up to 75 percent, most preferably up to 60 percent of the low molecular weight surfactant that is typically included in a personal care composition to obtain the above-mentioned viscosity is replaced by a water-soluble polymer to prepare a modified personal care composition.

Preferably the weight ratio between the low molecular weight surfactant and the water-soluble polymer is from 50:1 to 1:2, more preferably from 25:1 to 1:1, most preferably from 10:1 to 2:1. The total amount of the low molecular weight surfactant and the water-soluble polymer in the modified personal care composition should be chosen such that the composition has a viscosity of at least 50 mPa·s, and preferably a viscosity within the range indicated above.

The concentration of the low molecular weight surfactant in the modified personal care composition preferably is from 1 to 15 percent, more preferably from 2 to 10 percent, most preferably from 5 to 10 percent, based on the total weight of the composition. The concentration of the water-soluble polymer preferably is from 0.2 to 12 percent, more preferably from 0.3 to 10 percent, most preferably from 1 to 5 percent, based on the total weight of the modified composition.

The term "a low molecular weight surfactant" as used herein also encompasses a combination of two or more different types of surfactants. The low molecular weight surfactant used in the present invention has a weight-average molecular weight Mw of up to 8000, preferably up to 5000, more preferably up to 2000. The most preferred surfactants are non-polymeric, more preferably monomeric, compounds with a molecular weight of up to 1000, preferably up to 700. The weight average molecular weight can be determined by light scattering according to the Standard Test Method ASTM D-4001-93 (1999). Useful low molecular weight surfactants are generally compounds with a hydrophilic head and a hydrophobic end. Anionic, cationic, amphoteric and nonionic surfactants are useful.

As anionic surfactants preferably one or more substances from the group of carboxylic acids, carboxylic half-esters, sulfonic acids, preferably from the group of fatty acids, fatty alkylsulfuric acids and alkylarylsulfonic acids; sulfuric acid half-esters of long chain alcohols, alkylethersulfonic acids, like the alkylsulfuric acids; alkanesulfonic acids, or olefin-sulfonic acids may be used. Alkali metal salts, preferably the sodium or potassium salts; or ammonium salts of the listed acids are also useful. Accordingly, an alkali metal salt, particularly the sodium salt, is also meant each time in the present description a free acid is mentioned. To achieve adequate surface-active properties, the compounds should have long-chain hydrocarbon radicals, thus have at least 6 carbon atoms in the alkyl or alkenyl radical. Usually the carbon chains in the anionic surfactants contain 6 to 40, preferably 8 to 30, and more preferably 12 to 22 carbon atoms. Preferred carboxylic acids are hexanoic acid (caproic acid), heptanoic acid (enanthic acid), octanoic acid (caprylic acid), nonanoic acid (pelargonic acid), decanoic acid (capric acid), or undecanoic acid. More preferably fatty acids are used, such as dodecanoic acid (lauric acid), tetradecanoic acid (myristic acid), hexadecanoic acid (palmitic acid), octadecanoic acid (stearic acid), eicosanoic acid (arachic acid), docosanoic acid (behenic acid), tetraconsanoic acid (lignoceric acid), hexacosanoic acid (cerotic acid), triacotanoic acid (melissic acid), and the unsaturated species 9c-hexadecenoic acid (palmitoleic acid), 6c-octadecenoic acid (petroselic acid), 6t-octadecenoic acid (petroselaidic acid), 9c-octadecenoic acid (olaic acid), 9t-octadecenoic acid (elaidic acid), 9c,12c-octadecadienoic acid (linoleic acid), 9t,12t-octadecadienoic acid (linolaidic acid), and 9c,12,15c-octadecatrienoic acid (linolenic acid). Also mixtures of fatty acids are useful, such as coconut oil fatty acid, palm kernel oil fatty acid, tallow fatty acid, hardened tallow fatty acids, palmitic/stearic acid mixtures and soybean oil fatty acid. Alkylphosphates, sulfuric acid half-esters of long chain alcohols, alkylethersulfonic acids, like the alkylsulfuric acids; alkanesulfonic acids, olefinsulfonic acids or alkylbenzenesulfonates, preferably linear alkylbenzenesulfonates are also useful anionic surfactants. Alkanesulfonic acids can contain the sulfonic acid group terminally bound (primary alkanesulfonic acids) or along the C chain (secondary alkanesulfonic acids). Fatty alkyl sulfates, such as sodium octyl, decyl, lauryl, tetradecyl, hexadecyl, heptadecyl, or octadecyl sulfate; and salts of alkarylsulfonic acids, such as sodium octylbenzene sulfonates, are preferred. Other useful anionic surfactants are those of the general formula $R(OCH_2CH_2)_nOSO_3M$, wherein R is a $C_{10}$ to $C_{18}$ alkyl group, n is 1 to 3 and M is sodium; and salts of dialkyl sulfosuccinic acids, such as sodium dioctyl sulfosuccinate. A preferred anionic surfactant is sodium lauryl ether 2 EO sulfate wherein EO means a unit derived from ethylene oxide.

Useful nonionic surfactants are, for example, alkoxylated, advantageously ethoxylated, especially primary alcohols with preferably 8 to 18 carbon atoms and an average of 1 to 12 mols ethylene oxide (EO) per mol alcohol, wherein the alcohol radical may be linear or preferably branched in 2-position with methyl, or may contain linear and methyl-branched radicals in a mixture, as customarily occurs in oxoalcohol radicals. In particular, however, alcohol ethoxylates with linear radicals made from alcohols of native origin with 12 to 18 carbon atoms, for example from coconut, palm, tallow fatty, or oleyl alcohols are preferred, and an average of 2 to 8 EO per mol alcohol. Preferred ethoxylated alcohols include, for example, $C_{12-14}$-alcohols with 3 EO or 4 EO, $C_{9-11}$-alcohols with 7 EO, $C_{13-15}$-alcohols with 3 EO, 5 EO, 7 EO or 8 EO, $C_{12-18}$-alcohols with 3 EO, 5 EO or 7 EO and mixtures of these, such as mixtures of $C_{12-14}$-alcohols with 3 EO and $C_{12-18}$-alcohols with 5 EO. The indicated degrees of ethoxylation represent statistical mean values that may be an integer or a fraction for a specific product. In addition to these nonionic surfactants, fatty alcohols with more than 12 EO may also be used. Examples are tallow fatty alcohols with 14 EO, 25 EO, 30 EO or 40 EO. Other preferred nonionic surfactants are ethoxylated reaction products of $C_{8-22}$-fatty alcohols, preferably $C_{12-20}$-fatty alcohols, and especially $C_{14-18}$-fatty alcohols with 1 to 30 mols ethylene oxide, preferably 2 to 20 mols ethylene oxide, and especially 5 to 10 mols ethylene oxide. An additional class of preferably used nonionic surfactants is alkoxylated, preferably ethoxylated or ethoxylated and propoxylated fatty acid alkylesters, preferably with 1 to 4 carbon atoms in the alkyl chain, especially fatty acid methyl esters. An additional class of useful nonionic surfactants is the alkylpolyglycosides (APG). Preferred alkylpolyglycosides have the general formula $RO(G)_z$, in which R represents a linear or branched, especially methyl-branched in 2-position, saturated or unsaturated aliphatic radical with 8 to 22, preferably 12 to 18 C-atoms and G is the symbol that represents a glycose unit with 5 or 6 C-atoms, preferably glucose. The glycosidation degree z here is from 1.0 to 4.0, preferably from 1.0 to 2.0, and especially from 1.1 to 1.5. Preferably used are linear alkylpolyglucosides, thus alkylpolyglycosides in which the polyglycol radical is a glucose radical and the alkyl radical is an n-alkyl radical. An additional class of suitable nonionic surfactants are polyhydroxy fatty acid amides of Formula $R-CO-N(R^1)-[Z]$, wherein R—CO represents an aliphatic acyl radical with 6 to 22 carbon atoms, $R^1$ represents hydrogen, an alkyl or hydroxyalkyl radical with 1 to 4 carbon atoms and [Z] represents a linear or branched polyhydroxyalkyl radical with 3 to 10 carbon atoms and 3 to 10 hydroxyl groups.

Useful cationic surfactants have cationic hydrophobic residues and counter-cations, such as chloride, sulfate, or acetate. Examples include tetraalkyl ammonium chlorides, aryl trialkyl ammonium chlorides, tetraalkyl ammonium bromides, aryl trialkyl ammonium bromides or N-alkylpyridinium chloride.

Amphoteric surfactants have zwitterionic hydrophilic groups. Examples thereof include aminocarboxylic acids, betaines, and sulfobetaines.

The low molecular weight surfactant is at least partially replaced by a water soluble polymer in the personal care composition. The water soluble polymer has a solubility in water of at least 1 grams, more preferably at least 3 grams, most preferably at least 5 grams in 100 grams of distilled water at 25° C. and 1 atmosphere. The water-soluble polymer preferably has a surface tension of less than 65 mN/m², more preferably less than 60 mN/m², most preferably less than 55 mN/m², measured as a 0.2 weight percent aqueous solution at 25° C., measured using a Kruss Tensiometer (model K14, Kruss USA, Charlotte, N.C., USA).

The water-soluble polymer is preferably selected from one or more polysaccharides, gelatins, poly(amino acids), such as poly(aspartic acid) or poly(glutamic acid); polylactic acid or a salt of such a polymerized acid or one or more synthetic polymers selected from the group consisting of polyalkylene oxides, such as ethylene oxide homo- and copolymers having a weight average molecular weight of at least 10,000, and homo- and copolymers comprising in polymerized form an unsaturated acid or a salt thereof, such as acrylic acid, methacrylic acid, or a salt thereof, an unsaturated amide, such as acrylamide; a vinyl ester, a vinylalcohol, an acetate, such as vinylacetate; an alkylene imine, such as ethylene imine; an oxyethylene alkylether, a vinylpyrrolidone, vinyloxazolidone, vinylmethyloxazolidone, ethylene sulfonic acid, a vinylamine, vinylpyridine, an ethylenically unsaturated sulfate or sulfonate or a combination of one or more of these polymers.

The water-soluble polymer preferably is a polysaccharide. Examples of polysaccharides include gum arabic, xanthan gum, gum karaya, gum tragacanth, gum ghatti, carrageenan, dextran, alginates, agar, gellan gum, galactomannans such as guar gum, pectins, starches, starch derivatives, guar derivatives and xanthan derivatives. Starch derivatives, guar derivatives and xanthan derivatives are described in more detail in European patent EP 0 504 870 B, page 3, lines 25-56 and page 4, lines 1-30. Useful starch derivatives are for example starch ethers, such as hydroxypropyl starch or carboxymethyl starch. Useful guar derivatives are for example carboxymethyl guar, hydroxypropyl guar, carboxymethyl hydroxypropyl guar or cationized guar. Preferred hydroxypropyl guars and the production thereof is described in U.S. Pat. No. 4,645,812, columns 4-6. Preferred polysaccharides are cellulose esters or cellulose ethers. Preferred cellulose ethers are carboxy-$C_1$-$C_3$-alkyl celluloses, such as carboxymethyl celluloses; carboxy-$C_1$-$C_3$-alkyl hydroxy-$C_1$-$C_3$-alkyl celluloses, such as carboxymethyl hydroxyethyl celluloses; $C_1$-$C_3$-alkyl celluloses, such as methylcelluloses; $C_1$-$C_3$-alkyl hydroxy-$C_{1-3}$-alkyl celluloses, such as hydroxyethyl methylcelluloses, hydroxypropyl methylcelluloses or ethyl hydroxyethyl celluloses; hydroxy-$C_{1-3}$-alkyl celluloses, such as hydroxyethyl celluloses or hydroxypropyl celluloses; mixed hydroxy-$C_1$-$C_3$-alkyl celluloses, such as hydroxyethyl hydroxypropyl celluloses, or alkoxy hydroxyethyl hydroxypropyl celluloses, the alkoxy group being straight-chain or branched and containing 2 to 8 carbon atoms. Most preferably, the personal care composition comprises a water-soluble cellulose ether, such as a methylcellulose with a methyl degree of substitution $DS_{methoxyl}$ of from 1.2 to 2.2, preferably from 1.5 to 2.0, or a hydroxypropyl methylcellulose with a $DS_{methoxyl}$ of from 0.9 to 2.2, preferably from 1.1 to 2.0 and a $MS_{hydroxypropoxyl}$ of from 0.02 to 2.0, preferably from 0.1 to 1.2.

The viscosity of the water-soluble polymer generally is up to 100,000 mPa*s, preferably up to 25,000 mPa*s, more preferably up to 15,000 mPa*s, measured as a 2-wt. % aqueous solution at 25° C. using an Ubbelohde viscometer.

The water-soluble polymer generally has a weight average molecular weight of at least 10,000, preferably at least 12,000, more preferably at least 15,000, most preferably at least 18,000. The preferred upper limit for the weight average molecular weight largely depends on the type of polymer. Generally the weight average molecular weight of the water-soluble polymer is up to 5,000,000, preferably up to 500,000, more preferably up to 100,000. The weight average molecular weight can be determined by light scattering according to the Standard Test Method ASTM D-4001-93 (1999).

The use of the water-soluble polymer as a substitute for at least a portion of the low molecular weight surfactant in the personal care composition significantly improves the deposition of a benefit agent, such as a fragrance, on a substrate, such as hair or skin, and the headspace concentration of a fragrance without lowering the viscosity of the composition to less than 50 mPa*s.

A wide variety of one or more benefit agents can be comprised in the personal care composition, such as a fragrance, a biocontrol agent, a sunscreen agent, a moisturizing agent, an emollient, or a combination thereof. These benefit agents are known in the art. Preferred benefit agents are listed below, but their list is not comprehensive.

Fragrance includes spices or flavor enhancers which contribute to the overall flavor perception of the composition, such as perfumes or perfume raw materials. The fragrance is typically volatile and has a boiling point of up to 250° C. A disclosure of suitable perfume raw materials, traditionally used in perfumery, can be found in "Perfume and Flavor Chemicals", Vol. I and II, S. Arctander, Allured Publishing, 1994, ISBN 0-931710-35-5. Examples of fragrance are essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, thymol, spirantol, penene, limonene and terpenoid oils.

Biocontrol agents include, for example, biocides, antimicrobials, bactericides, fungicides, algaecides, mildeweides, disinfecticides, sanitizer-like bleaches, antiseptics, insecticides, insect or moth repellant, vermicides, plant growth hormones and combinations thereof. Typical antimicrobials include glutaraldehyde, cinnamaldehyde and mixtures thereof. Typical insect and moth repellants are perfume ingredients, such as citronellal, citral, N,N-diethyl meta toluamide, Rotundial, 8-acetoxycarvotanacenone, and mixtures thereof.

Preferred emollients or moisturizing agents are glycerin, triglyceride oils, mineral oils, petrolatum, and mixtures thereof, more preferably triglycerides such as sunflower seed oil. Examples of useful emollients are also disclosed in the published patent application WO 03/075879 on page 3, lines 18-31 and page 4, lines 1-11, the teaching of which is incorporated herein by reference.

Examples of useful sunscreen agents are octyl methoxyl cinnamate (Parsol MCX) and butyl methoxy benzoylmethane (Parsol 1789). Other examples of useful sunscreen agents are disclosed in the published patent application WO 03/075879 on page 4, lines 15-31 and on page 5, the teaching of which is incorporated herein by reference.

Other preferred water-insoluble benefit agents are (a) silicone oils and modifications thereof such as linear and cyclic polydimethylsiloxanes; amino, alkyl, alkylaryl, and aryl silicone oils; (b) fats and oils including natural fats and oils, preferably plant fats and oils, such as jojoba, soybean, sunflower, rice bran, avocado, almond, olive, sesame, persic, castor, coconut and mink oils; cacao fat; and animal fats and oils, such as beef tallow and lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) plant extracts; (e) hydrocarbons such as liquid paraffins, vaseline, microcrystalline wax, ceresin, squalene, pristan and mineral oil; (f) higher alcohols such as lauryl, cetyl, stearyl, oleyl, behenyl, cholesterol and 2-hexydecanol alcohol; (g) lipids such as cholesterol, ceramides, sucrose esters and pseudoceramides as described in European Patent Specification No. 556,957; (h) vitamins, minerals, and skin nutrients such as milk, vitamins A, E, and K; vitamin alkyl esters, including vitamin C alkyl esters; magnesium, calcium, copper, zinc and other metallic components; (i) antiaging compounds, such as alpha hydroxy acids, beta hydroxy acids; or combinations of the listed benefit agents.

As indicated above, the personal care composition is water-based. However, it can also comprise one or more organic diluents such as ethyl alcohol, isopropyl alcohol, higher alcohols or propylene glycol. If one or more organic diluents are present, their concentration generally is not more than 20 percent, preferably not more than 10 percent, most preferably not more than 5 percent, based on the total weight of the personal care composition.

The personal care composition can be a leave-on product, but the present invention is particularly useful for wash-off products. Useful personal care compositions are oral care, hair care or skin care compositions, particularly hair or skin care compositions, most preferably shampoos, shower gels, cleansers, bubble baths and body wash formulations.

The following examples are for illustrative purposes only and are not intended to limit the scope of the present invention. All percentages are by weight unless otherwise specified.

EXAMPLES 1-14 AND COMPARATIVE EXAMPLES A-K

Hair and skin care compositions are prepared with the components listed in the Tables below.

The components of the compositions listed in the Tables below are the following:

Low Molecular Weight Surfactants:
SLES-2: Sodium laureth sulfate with 2 EO units wherein EO means a unit derived from ethylene oxide;
Sodium lauryl sulfate;
Cocamidopropyl betaine;
Disodium cocamphodiacetate;
CEMA: Cocamide MEA (cocoyl Monoethanol amine), commercially available from Uniqema; and
APG: Alkyl Polyglycoside, commercially available from Henkel as Plantaren 2000. Perfumes and other benefit agents:
Perfume 1: White Tea Mod 4 Fragrance oil from Fragrance Resources Inc. (Bloomfield, N.J., USA).
Perfume 2: Musk Fragrance Oil from Fragrance Resources Inc. (Bloomfield, N.J., USA).
Perfume 3: Citrus Fragrance Oil from Fragrance Resources Inc. (Bloomfield, N.J., USA).
Salicylic Acid: Purchased from Aldrich.
Triclosan: It is commercially available from Ciba Specialty Chemicals under the Trademark IRGASAN DP 300.

Water-soluble polymers:
METHOCEL E3LV: Hydroxypropyl methylcellulose with a methoxyl substitution of 28-30 percent, a hydroxypropoxyl substitution of 7-12 percent and a viscosity of about 3 mPa·s. It is commercially available from The Dow Chemical Company under the Trademark METHOCEL E3LV.
METHOCEL 40-100: Hydroxypropyl methylcellulose with a methoxyl substitution of 18-21 percent, a hydroxypropoxyl substitution of 23-31 percent and a viscosity of about 12,000 mPa·s. It is commercially available from The Dow Chemical Company under the Trademark METHOCEL 40-100.
METHOCEL E50: Hydroxypropyl methylcellulose with a methoxyl substitution of 28-30 percent, a hydroxypropoxyl substitution of 7-12 percent and a viscosity of about 50 mPa·s. It is commercially available from The Dow Chemical Company under the Trademark METHOCEL E50.
METHOCEL 40-202: Hydroxypropyl methylcellulose with a methoxyl substitution of 28-30 percent, a hydroxypropoxyl substitution of 7-12 percent and a viscosity of about 4000 mPa·s. It is commercially available from The Dow Chemical Company under the Trademark METHOCEL 40-202.
The viscosities of the METHOCEL cellulose ethers are measured a 2 weight percent aqueous solution at 25° C. using an Ubbelohde viscometer.
POLYOX WSR N-60K: Polyethylene oxide with 2% solution viscosity of 2000-4000 mPa·s, measured as a 2 wt. % aqueous solution at 25° C. using an Ubbelohde viscometer. It is commercially available from The Dow Chemical Company under the Trademark POLYOX N-60K.

CELLOSIZE PCG-10: Hydroxyethyl cellulose with a viscosity of 4400-6000 cP, measured as a 1% aqueous solution at 25° C. with a Brookfield LVF No. 4 spindle. It is commercially available from The Dow Chemical Company under the Trademark CELLOSIZE PCG-10.

The perfume headspace concentration is measured as follows: 5 grams of the hair and skin care composition is weighed into a 10 mL headspace vial. The vial is left to equilibrate at room temperature for two days. 500 microliters of headspace is injected into a Hewlett Packard 6890 gas chromatograph (GC) and all the peaks are tabulated for comparison. The GC conditions are: 30 meter J & W Scientific Durabond-5×0.32 mm ID×0.25 μm film thickness (J & W Scientific, Bellefonte, Pa.); helium constant gas flow of 2 ml/min; temperature profile: 60° C. for 2 minutes, heating 6 degrees/min to 230° C. and hold there for 10 minutes; Injection port 250° C.; flame ionization detector 275° C.; the sample temperature is 35° C.

In-vitro skin is used as a substrate for the perfume deposition study. A 3 cm×6 cm size skin is used. The in-vitro skin is wetted with water and 0.15 ml of a composition listed in Table 1 below is applied. The composition is spread on the skin surface for 30 seconds and then rinsed for 15 seconds. The rinsing water flow rate is 1 liter/min with a temperature of 28-32° C. The in-vitro skin is then placed in a glass vial and 2 grams of heptane are added to extract the perfume deposited on the skin. One microliter of the extract is injected into a GC. The peak area is recorded. A standard of 125 ppm perfume in 50/50 water/isopropanol is prepared for comparison to the samples. The peak area of the standard is compared with the peak area of the sample (external standard calculation).

The GC conditions are: Restek RTX-5MS 15 meter×0.25 mm ID×0.25 μm film thickness (Restek Bellefonte, Pa.); temperature profile: 60° C. for 2 minutes, then 10° C. per minute to 275° C. and hold there for 5 minutes, head pressure 8 psi (55 kPa); inlet temperature 250° C., flame ionization detector 250° C., detector make up flow (helium) 20 mL/minute.

TABLE 1

| Composition | Comp. Example A (%) | Example 1 (%) | Example 2 (%) |
|---|---|---|---|
| SLES-2 | 11 | 5.5 | 5.5 |
| cocamidopropyl betaine | 4 | 2 | 2 |
| Perfume 1 | 1 | 1 | 0.75 |
| Methocel E3LV | 0 | 3 | 3 |
| Water | 84 | 88.5 | 88.75 |
| Perfume headspace (arbitrary unit) | 22.3 | 37.1 | 26 |
| Perfume deposition (ppm) | 13 | 22 | 18 |

The comparison between Examples 1 or 2 and Comparative Example A illustrates that personal care compositions wherein a part of the low molecular weight surfactant is substituted by a water-soluble polymer shows a significant improvement for both perfume headspace concentration and benefit agent deposition, such as perfume deposition. Although the composition of Example 2 has a perfume concentration in the liquid personal care composition which is 25 percent less than in the composition of Comparative Example A, the overall perfume benefit, that means the perfume headspace concentration and the perfume deposition, is significantly better in the composition of Example 2 than in the composition of Comparative Example A.

The viscosity of water-based personal care compositions wherein a part of the low molecular weight surfactant is substituted by a water-soluble polymer is also tested. The viscosity is measured at 25° C. using a Brookfield viscometer (model: LVDVII, Brokfield Engineering Laboratories Inc., Stoughton, Md., USA). The compositions and the results are listed in Table 2.

TABLE 2

| Composition | Comp. Example B (%) | Comp. Example C (%) | Example 3 (%) |
|---|---|---|---|
| SLES-2 | 11 | 5.5 | 5.5 |
| cocamidopropyl betaine | 4 | 2 | 2 |
| Methocel 40-100 | 0 | 0 | 1 |
| Sodium Chloride | 1.5 | 0.75 | 1.5 |
| Water | 83.5 | 91.75 | 90 |
| Product viscosity (mPa · s) | 18300 | 3 | 10200 |

The results in Table 2 illustrate that a substantial portion of the low molecular weight surfactant can be replaced by a water-soluble polymer for improving the deposition of a benefit agent on a substrate or for increasing the headspace concentration of a fragrance without lowering the viscosity of the composition to an unsatisfactory level.

Table 3 below shows the results of a sensory study for testing perfume headspace. Ten panelists were asked to select which formulation has stronger perfume headspace between Comparative Example D and Example 4 or 5. The results clearly illustrate that the compositions used in the present invention which comprise a water-soluble polymer as a substitute for a portion of the low molecular weight surfactant have a higher perfume headspace concentration than a comparative composition which does not comprise a water-soluble polymer as a partial substitute for the low molecular weight surfactant.

TABLE 3

| Composition | Comp. Example D (%) | Example 4 (%) | Example 5 (%) |
|---|---|---|---|
| Sodium Lauryl Sulfate | 5.5 | 3 | 3.4 |
| SLES-2 | 7 | 4 | 4.8 |
| cocamidopropyl betaine | 2.5 | 1.5 | 1.8 |
| NaCl | 1.1 | 1.5 | 1.5 |
| Perfume 1 | 1 | 1 | 1 |
| Methocel E50 | 0 | 2 | 2 |
| Water | 82.9 | 87 | 85.5 |
| Product viscosity (mPa * s) | 48000 | 10530 | 15000 |

| Sensory Study 1 | Number of Panelists | Sensory Study 2 | Number of Panelists |
|---|---|---|---|
| Comp. Example D has stronger perfume headspace | 1 | Comp. Example D has stronger perfume headspace | 2 |
| Example 3 has stronger perfume headspace | 9 | Example 4 has stronger perfume headspace | 8 |

Tables 4-7 below show the results of sensory studies for testing perfume headspace of hair care and skin compositions comprising other fragrances, other types and concentrations of water-soluble polymers and other surfactant systems. Also these results clearly illustrate that the compositions used in the present invention which comprise a water-soluble polymer as a substitute for a portion of the low molecular weight surfactant have a stronger perfume headspace than a comparative composition which does not comprise a water-soluble polymer as a partial substitute for the low molecular weight surfactant.

TABLE 4

| Composition | Comp. Example E (%) | Example 6 (%) |
|---|---|---|
| Sodium Lauryl Sulfate | 5.5 | 3 |
| SLES-2 | 7 | 4 |
| cocamidopropyl betaine | 2.5 | 1.5 |
| NaCl | 1.1 | 1.5 |
| Perfume 2 | 1 | 1 |
| Methocel E50 | 0 | 2 |
| Water | 82.9 | 87 |
| Product viscosity (mPa * s) | 46000 | 10020 |

| Sensory Study | Number of Panelists |
|---|---|
| Comparative Example E has stronger perfume headspace | 1 |
| Example 6 has stronger perfume headspace | 9 |

TABLE 5

| Composition | Comp. Example F (%) | Example 7 (%) | Example 8 (%) |
|---|---|---|---|
| SLES-2 | 11 | 5.5 | 5.5 |
| cocamidopropyl betaine | 4 | 2 | 2 |
| NaCl | 1.5 | 1.5 | 1.5 |
| Perfume 1 | 1 | 1 | 1 |
| CELLOSIZE PCG-10 | 0 | 1 | 0 |
| POLYOX N-60K | 0 | 0 | 1 |
| Water | 82.5 | 89 | 89 |

| Sensory Study 1 | Number of Panelists | Sensory Study 2 | Number of Panelists |
|---|---|---|---|
| Comp. Example F has stronger perfume headspace | 3 | Comp. Example F has stronger perfume headspace | 2 |
| Example 7 has stronger perfume headspace | 7 | Example 8 has stronger perfume headspace | 8 |

TABLE 6

| Composition | Comp. Example G (%) | Example 9 (%) | Example 10 (%) |
|---|---|---|---|
| SLES-2 | 11 | 5.5 | 5.5 |
| cocamidopropyl betaine | 4 | 2 | 2 |
| NaCl | 1.5 | 1.5 | 1.5 |
| Perfume 1 | 1 | 1 | 1 |
| METHOCEL 40-202 | 0 | 1 | 0.5 |
| Water | 82.5 | 89 | 89.5 |

| Sensory Study 1 | Number of Panelists | Sensory Study 2 | Number of Panelists |
|---|---|---|---|
| Comp. Example G has stronger perfume headspace | 2 | Comp. Example G has stronger perfume headspace | 2 |
| Example 9 has stronger perfume headspace | 8 | Example 10 has stronger perfume headspace | 8 |

TABLE 7

| Composition | Comp. Example H (%) | Example 11 (%) |
|---|---|---|
| Disodium Cocamphodiacetate | 2.6 | 1.3 |
| SLES-2 | 15.5 | 7.75 |
| Perfume 3 | 1 | 1 |
| Methocel 40-202 | 0 | 1 |
| Water | 80.9 | 88.95 |

| Sensory Study | Number of Panelists |
|---|---|
| Comparative Example H has stronger perfume headspace | 1 |
| Example 11 has stronger perfume headspace | 9 |

Salicylic Acid Deposition Study

A 3 cm×6 cm size in-vitro skin is used as a substrate for the salicylic acid deposition study. The in-vitro skin is wetted with water and 0.15 ml of a composition as listed in Table 8 below. The composition is spread on the skin surface for 30 seconds and then rinsed for 15 seconds. The rinsing water flow rate is 1 liter/min with a temperature of 28-32° C. The in-vitro skin is then placed in a glass vial and 10 grams of isopropyl alcohol/water (50:50 by weight) are added to extract the salicylic acid deposited on the skin. 10 microliters of the extract solution are injected on a 250 mm×4.6 μm Luna 5 C8 (2) liquid chromatography column connected to a UV detector (280 wavelength). The area of the salicylic acid is recorded and its concentration is calculated using the standard calibration curve. The liquid chromatograph is a Waters 2690 Liquid Chromatograph (HPLC), Waters Corp., Milford, Mass.

The HPLC conditions are: samples are filtered using a 0.45 micron filter and analyzed using HPLC and each one injected twice. Mobile phase: 25% (v/v) acetonitrile in water; column: Luna 5 micron C8 250×4.60 mm Phenomenex, Torrance, Calif. Injection: 10 microliters; flow: 1 mL/min; detector: UV/V is 280 nm The results are listed in Table 8 below:

TABLE 8

| Composition | Comp. Example I (%) | Example 12 (%) |
|---|---|---|
| Neutragena Anti-acne Facial cleanser containing 2% salicylic acid | 100 | 50 |
| Added salicylic acid | 0 | 1 |
| Methocel 40-202 | 0 | 1 |
| Water | 0 | 48 |
| Salicylic acid deposition (ppm) | 39.5 | 65.5 |

The comparison between Examples 12 and Comparative Example I illustrates that personal care compositions wherein a part of the low molecular weight surfactant is substituted by a water-soluble polymer shows a significant improvement for benefit agent deposition, such as salicylic acid. Both formulations contain 2% salicylic acid.

Color Fading Study

European single-bleached hair tresses (International Hair Importers & Products Inc., Glendale, N.Y.) is used in this study. Hair tresses are dyed with a commercial product from L'Oreal (Couleur Experte 6.6, Cherry Cordial, Bright Auburn) following product instructions provided in the product.

Hair tresses are washed multiple times to assess their color fading properties. 1.0 g of the shampoo in Table 9 below is applied to the hair tresses for one minute followed by rinsing under tap water for 1 minute. Hair tresses are hung vertically and air-dried before repeating the treatment with the shampoo. Hair tresses are washed with the shampoo five times before conducting sensory panel evaluation. The results are listed in Table 9 below.

TABLE 9

| Composition | Comp. Example J (%) | Example 13 (%) |
|---|---|---|
| Schwarzkopf Gliss Kur Color Safe Shampoo | 100 | 60 |
| Methocel 40-202 | 0 | 1 |
| Water | 0 | 39 |

| Sensory Study | Number of Panelists |
|---|---|
| Hair tress washed with Comp. Example J has darker color | 1 |
| Hair tress washed with Example 13 has darker color | 9 |

The comparison between Example 13 and Comparative Example J illustrates that personal care compositions wherein a part of the low molecular weight surfactant is substituted by a water-soluble polymer shows a significant improvement in color fading properties of the personal care compositions, such as shampoo formulations.

Triclosan Deposition Study

A composition as listed in Table 10 below is used for a triclosin deposition study on a 3 cm×6 cm size in-vitro skin. The composition is applied and extracted in the same way as in the salicylic acid deposition study.

10 microliters of the extract solution is injected on a 250 mm×4.6 μm Luna 5 C8 (2) liquid chromatography column connected to a UV detector (279 wavelength). The area of the triclosan is recorded and triclosan concentration is calculated using a standard calibration curve. The results are listed in Table 10 below.

Standards are prepared by making a stock solution of triclosan (613 ppm) in ethanol and then serial dilutions from that.

HPLC: Waters 2690 Liquid Chromatograph, Waters Corp., Milford, Mass.

Mobile phase: The used mobile phase is a solvent mixture with gradient specific in the table below. Column: Luna 5 micron C8 250×4.60 mm Phenomenex, Torrance, Calif.; Injection: 10 microliters; Flow: 1 mL/min; Detector: UV/V is 280 nm HPLC Conditions:

| Time (minutes) | Flow (mls/minute) | % Acetonitrile | % Water |
|---|---|---|---|
| 1 | 1 | 70 | 30 |
| 10 | 1 | 100 | 0 |
| 20 | 1 | 100 | 0 |
| 21 | 1 | 100 | 0 |
| 40 | 1 | 70 | 30 |
| 41 | 0 | 70 | 30 |

TABLE 10

| Composition | Comp. Example K (%) | Example 14 (%) |
|---|---|---|
| SLES-2 | 7.6 | 3.8 |
| cocamidopropyl betaine | 1.25 | 0.62 |
| APG | 2.6 | 1.3 |
| CEMA | 1.8 | 0.9 |
| triclosan | 0.3 | 0.3 |
| Methocel 40-202 | 0 | 1 |
| Water | 86.45 | 92.08 |
| triclosan deposition (ppm) | 1.8 | 2.4 |

The comparison between Example 14 and Comparative Example K illustrates that personal care compositions wherein a part of the low molecular weight surfactant is substituted by a water-soluble polymer shows a significant improvement for benefit agent deposition, such as triclosan.

What is claimed is:

1. A method of increasing the headspace concentration of a fragrance provided by a water-based personal care composition having a viscosity of at least 50 mPa·s at 25° C. and comprising the fragrance and a low molecular weight surfactant, which method comprises:

formulating the personal care composition with an amount of low molecular weight surfactant that is insufficient to achieve the viscosity and incorporating a water-soluble polymer in the personal care composition as a substitute for at least a portion of the amount of the low molecular weight surfactant that would have been required to achieve the viscosity, and wherein the water-soluble polymer is a cellulose ether that has a surface tension of less than 55 mN/m$^2$, measured as a 0.2 weight percent aqueous solution at 25° C.

2. The method of claim 1 wherein the water-soluble polymer is a substitute for at least 20 percent of the low molecular weight surfactant.

3. The method of claim 1 wherein the cellulose ether is a water-soluble cellulose ether having a viscosity of up to 25,000 mPa·s, measured as a 2 weight percent aqueous solution at 25° C.

4. The method of claim 1 wherein the weight ratio between the low molecular weight surfactant to the water-soluble polymer is from 25:1 to 1:1.

5. The method of claim 1 wherein the concentration of the low molecular weight surfactant is from 2 to 10 percent and the concentration of the water-soluble polymer is from 0.3 to 10 percent, each percentage being based on the total weight of the personal care composition.

6. The method of claim 1 wherein the personal care composition comprises at least 80 percent water, based on the total weight of the composition.

7. The method of claim 1 wherein the water-soluble polymer is a carboxy-$C_1$-$C_3$-alkyl cellulose, a carboxy-$C_1$-$C_3$-alkyl hydroxy-$C_1$-$C_3$-alkyl cellulose, a $C_1$-$C_3$-alkyl cellulose, a $C_1$-$C_3$-alkyl hydroxy-$C_1$-$C_3$-alkyl cellulose, a hydroxy-$C_1$-$C_3$-alkyl cellulose, a mixed hydroxy-$C_1$-$C_3$-alkyl cellulose, or an alkoxy hydroxyethyl hydroxypropyl cellulose, the alkoxy group being straight-chain or branched and containing 2 to 8 carbon atoms.

* * * * *